US010480002B2

(12) United States Patent
Chen (10) Patent No.: US 10,480,002 B2
(45) Date of Patent: *Nov. 19, 2019

(54) ALGAL BASED EDIBLE VACCINES

(71) Applicant: TRANSALGAE ISRAEL LTD., Rehovot (IL)

(72) Inventor: Ofra Chen, Rehovot (IL)

(73) Assignee: TRANSALGAE ISRAEL LTD., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/116,567

(22) PCT Filed: Feb. 12, 2015

(86) PCT No.: PCT/IL2015/050166
§ 371 (c)(1),
(2) Date: Aug. 4, 2016

(87) PCT Pub. No.: WO2015/121863
PCT Pub. Date: Aug. 20, 2015

(65) Prior Publication Data
US 2016/0346373 A1  Dec. 1, 2016

Related U.S. Application Data

(60) Provisional application No. 61/938,707, filed on Feb. 12, 2014.

(51) Int. Cl.
*C12N 15/82* (2006.01)
*A61K 39/12* (2006.01)
*A61K 39/112* (2006.01)
*A61K 36/00* (2006.01)
*A61K 39/00* (2006.01)

(52) U.S. Cl.
CPC ...... *C12N 15/8258* (2013.01); *A61K 39/0275* (2013.01); *A61K 39/12* (2013.01); *A61K 36/00* (2013.01); *A61K 2039/517* (2013.01); *A61K 2039/542* (2013.01); *A61K 2039/552* (2013.01); *C07K 2319/01* (2013.01); *C07K 2319/02* (2013.01); *C07K 2319/10* (2013.01); *C07K 2319/42* (2013.01); *C12N 2770/30034* (2013.01); *C12N 2800/22* (2013.01); *Y02A 50/482* (2018.01)

(58) Field of Classification Search
None
See application file for complete search history.

(56) References Cited

U.S. PATENT DOCUMENTS

| | | | |
|---|---|---|---|
| 6,379,677 B1 | 4/2002 | Klesius | |
| 7,204,993 B2 | 4/2007 | Evans | |
| 7,410,637 B2 | 8/2008 | Sayre | |
| 8,282,915 B2 | 10/2012 | Sayre | |
| 9,827,280 B2 * | 11/2017 | Moshitzky | A61K 38/27 |
| 2003/0066107 A1 | 4/2003 | Xue | |
| 2007/0148166 A1 | 6/2007 | Wu | |
| 2009/0098149 A1 * | 4/2009 | Sayre | A61K 39/05 424/184.1 |
| 2011/0014708 A1 | 1/2011 | Tsai | |
| 2011/0081706 A1 | 4/2011 | Schlesinger | |
| 2011/0165635 A1 | 7/2011 | Copenhaver | |
| 2013/0065314 A1 | 3/2013 | MacMillan | |
| 2014/0154806 A1 | 6/2014 | Schneider | |
| 2014/0234904 A1 | 8/2014 | Herbert | |
| 2018/0036357 A1 * | 2/2018 | Moshitzky | A61K 38/27 |

FOREIGN PATENT DOCUMENTS

| | | | | |
|---|---|---|---|---|
| CN | 1330718 A | 1/2002 | | |
| CN | 1778932 A | 5/2006 | | |
| CN | 101960013 A | 1/2011 | | |
| CN | 102559735 A | 7/2012 | | |
| JP | 6-505870 A | 7/1994 | | |
| JP | 2012-500640 A | 1/2012 | | |
| JP | 6275143 B2 | 2/2018 | | |
| WO | 92/16618 A1 | 10/1992 | | |
| WO | 1997039106 A1 | 10/1997 | | |
| WO | 0198335 A2 | 12/2001 | | |
| WO | 2002076391 A2 | 10/2002 | | |
| WO | WO 2005/112994 | * 12/2005 | ............. | A61K 39/12 |
| WO | 2008027235 A1 | 3/2008 | | |
| WO | 2011063284 A1 | 5/2011 | | |
| WO | 2012030759 A1 | 3/2012 | | |
| WO | 2014030165 A1 | 2/2014 | | |

OTHER PUBLICATIONS

Specht et al. Micro-algae come of age as a platform for recombinant protein production. (2010) Biotechnology Letters; vol. 32; pp. 1373-1383.*
Jiang et al. Membrane anchors for vacuolar targeting: application in plant bioreactors. (2002) Trends in Biotechnology; vol. 20; pp. 99-102.*
Becker et al. Evolution of vacuolar targeting in algae. (2009) Botanica Marina; vol. 52; pp. 117-128 (Year: 2009).*
Bowler et al. Endo-1,3-beta-glucosidase [Phaeodactylum tricornutum CCAP 1055/1]. (2009) Gen Bank Accession XP_002181321; pp. 1-2 (Year: 2009).*

(Continued)

*Primary Examiner* — Cathy Kingdon Worley (74) *Attorney, Agent, or Firm* — J.A. Lindeman & Co., PLLC; Jeffrey Lindeman; Sulay Jhaveri (57) ABSTRACT

Provided are edible vaccines including transgenic microalgae expressing at least one exogenous antigen or an intervening organism including the transgenic microalgae. The antigen expressing microalgae are used for oral delivery of the antigen to a target organism in its intact and functional form. The exogenous antigen, expressed in the microalgae, is characterized by exerting at least one immunogenic response in the subject consuming the vaccine.

15 Claims, 2 Drawing Sheets
Specification includes a Sequence Listing.

(56) References Cited

OTHER PUBLICATIONS

Nakamura et al. Protein targeting to the vacuole in plant cells. (1993) vol. 101; pp. 1-5 (Year: 1993).*

Dreesen et al., (2010) Heat-stable oral alga-based vaccine protects mice from *Staphylococcus aureus* infection. J Biotechnol 145(3): 273-280.

Gregory et al., (2013) Alga-produced cholera toxin-Pfs25 fusion proteins as oral vaccines. Appl Environ Microbiol 79(13): 3917-3925.

Khan et al., (2012) Using storage organelles for the accumulation and encapsulation of recombinant proteins. Biotechnol J 7(9): 1099-1108.

Kwon et al., (2013) Oral delivery of human biopharmaceuticals, autoantigens and vaccine antigens bioencapsulated in plant cells. Adv Drug Deliv Rev 65(6): 782-799.

Lin et al., (2007) An oral nervous necrosis virus vaccine that induces protective immunity in larvae of grouper (*Epinephelus coioides*). Aquaculture 268(1-4): 265-273.

Rasala et al., (2014) Enhanced genetic tools for engineering multigene traits into green algae. PLoS One 9(4):e94028; 8 pages.

Reinders et al., (2012) Evolution of plant sucrose uptake transporters. Front Plant Sci 3: 22; 12 pages.

Siripornadulsil et al., (2007) Microalgal Vaccines. In: León R., Galván A., Fernández E. (eds) Transgenic Microalge as Green Cell Factories. Advances in Experimental Medicine and Biology, vol. 616. Springer New York, NY; pp. 122-128.

Xiang et al., (2013) Vacuolar protein sorting mechanisms in plants. FEBS J 280(4): 979-993.

Apt et al., (1996) Stable nuclear transformation of the diatomPhaeodactylum tricornutum. Molecular and General Genetics MGG, 252(5), 572-579.

Bowler et al., Phaeodactylum tricocornutum CCAP 1055/1 endo-1,3-beta-glucosidase, mRNA; XM_002181285.1. From: http://www.ncbi.nlm.nih.gov/nuccore/XM_002181285.1; retrieved on Aug. 15, 2016; 2 pages.

Database UniprotKB/TrEMBL (online), Nov. 1, 1996 (Nov. 1, 1996). The ER Chaperon BiP from the diatom Phaeodactylum, Uniprot accession number: Q41074. URL: http://www.uniprot.org/uniprot/Q41074-.

Geng et al., (2012) *Steptococcus agalactiae*, an Emerging Pathogen for Cultured Ya-Fish, Schozothorax prenanti, in China. Transboundary and emerging diseases, 59(4), 369-375.

Hempel et al., (2011) Algae as protein factories: expression of a human antibody and the respective antigen in the diatom Phaeodactylum tricornutum. PLoS One, 6(12), e28424.

Kim et al., (2002) Stable integration and functional expression of flounder growth hormone gene in transformed microalga, Chlorella ellipsoidea. Mar Biotechnol (NY) 4(1): 63-73.

Nakai et al., (2009) Current Knowledge on Viral Nervous Necrosis (VNN) and its Causative Betanodaviruses. Israeli Journal of Aquaculture-Barnidgeh, 61(3), 198-207.

Patil et al., (2007) Fatty acid composition of 12 microalgae for possible use in aquaculture feed. Aquaculture International, 15(1), 1-9.

Poisa-Beiro et al., (2008) Nodavirus increases the expression of Mx and inflammatory cytokines in fish brain. Molecular immunology, 45(1), 218-225.

Richter et al., (2000) Production of hepatitis B surface antigen in transgenic plants for oral immunization. Nat Biotechnol 18(11): 1167-71.

Skrede et al., (2011) Evaluation of microalgae as sources of digestible nutrients for monogastric animals1. Journal of Animal and Feed Sciences, 20, 131-142.

Specht et al., (2014) Algae-based oral recombinant vaccines. Name: Frontiers in Microbiology, 5, 60.

Tague et al., (1990) A short domain of the plant vacuolar protein phytohemagglutinin targets invertase to the yeast vacuole. Plant Cell 2(6): 533-46.

GenBank Accession No. AF219942; Shuttle vector pPha-T1 complete sequence; Jun. 12, 2000; retrieved from: https://www.ncbi.nlm.nih.gov/nuccore/AF219942 Oct. 30, 2016, 2 Pages.

Kermode (1996) Mechanisms of Intracellular Protein Transport and Targeting in Plant Cells. Critical Reviews in Plant Sciences 15: 285-423.

Murray et al., (2002) Expression of biotin-binding proteins, avidin and streptavidin, in plant tissues using plant vacuolar targeting sequences. Transgenic Res 11(2): 199-214.

* cited by examiner

SEQUENCE LISTING

```
<160> NUMBER OF SEQ ID NOS: 14

<210> SEQ ID NO 1
<211> LENGTH: 22
<212> TYPE: PRT
<213> ORGANISM: Phaeodactylum tricornutum

<400> SEQUENCE: 1

Met Ser Ile Arg Leu Phe Ser Thr Ala Leu Leu Ala Ala Cys Leu Ala
1               5                   10                  15

Lys Ala Thr Ala Gln Thr
            20

<210> SEQ ID NO 2
<211> LENGTH: 33
<212> TYPE: PRT
<213> ORGANISM: Phaeodactylum tricornutum

<400> SEQUENCE: 2

Met Met Phe Met Arg Ile Ala Val Ala Ala Leu Ala Leu Leu Ala Ala
1               5                   10                  15
```

```
Pro Ser Ile Arg Ala Glu Glu Ala Gly Glu Ala Lys Met Gly Thr
            20                  25                  30
Val

<210> SEQ ID NO 3
<211> LENGTH: 338
<212> TYPE: PRT
<213> ORGANISM: Nervous necrosis virus

<400> SEQUENCE: 3

Met Val Arg Lys Gly Asp Lys Lys Leu Ala Lys Pro Ala Thr Thr Lys
1               5                   10                  15

Ala Ala Asn Pro Gln Pro Arg Arg Ala Asn Asn Arg Arg Arg Ser
            20                  25                  30

Asn Arg Thr Asp Ala Pro Val Ser Lys Ala Ser Thr Val Thr Gly Phe
            35                  40                  45

Gly Arg Gly Thr Asn Asp Val His Leu Ser Gly Met Ser Arg Ile Ser
        50                  55                  60

Gln Ala Val Leu Pro Ala Gly Thr Gly Thr Asp Gly Tyr Val Val Val
65                  70                  75                  80

Asp Ala Thr Ile Val Pro Asp Leu Leu Pro Arg Leu Gly His Ala Ala
                85                  90                  95

Arg Ile Phe Gln Arg Tyr Ala Val Glu Thr Leu Glu Phe Glu Ile Gln
            100                 105                 110

Pro Met Cys Pro Ala Asn Thr Gly Gly Gly Tyr Val Ala Gly Phe Leu
        115                 120                 125

Pro Asp Pro Thr Asp Asn Asp His Thr Phe Asp Ala Leu Gln Ala Thr
    130                 135                 140

Arg Gly Ala Val Val Ala Lys Trp Trp Glu Ser Arg Thr Val Arg Pro
145                 150                 155                 160

Gln Tyr Thr Arg Thr Leu Leu Trp Thr Ser Ser Gly Lys Glu Gln Arg
                165                 170                 175

Leu Thr Ser Pro Gly Arg Leu Ile Leu Leu Cys Val Gly Asn Asn Thr
            180                 185                 190

Asp Val Val Asn Val Ser Val Leu Cys Arg Trp Ser Val Arg Leu Ser
        195                 200                 205

Val Pro Ser Leu Glu Thr Pro Glu Glu Thr Thr Ala Pro Ile Met Thr
    210                 215                 220

Gln Gly Pro Leu Tyr Asn Asp Ser Leu Ser Thr Asn Asp Phe Lys Ser
225                 230                 235                 240

Ile Leu Leu Gly Ser Thr Pro Leu Asp Ile Ala Pro Asp Gly Ala Val
                245                 250                 255

Phe Gln Leu Asp Arg Pro Leu Ser Ile Asp Tyr Ser Leu Gly Thr Gly
            260                 265                 270

Asp Val Asp Arg Ala Val Tyr Trp His Leu Lys Lys Phe Ala Gly Asn
        275                 280                 285

Thr Gly Thr Pro Ala Gly Trp Phe Arg Trp Gly Ile Trp Asp Asn Phe
    290                 295                 300

Asn Lys Thr Phe Thr Asp Gly Val Ala Tyr Tyr Ser Asp Glu Gln Pro
305                 310                 315                 320

Arg Gln Ile Leu Leu Pro Val Gly Thr Val Cys Thr Arg Val Asp Ser
                325                 330                 335

Glu Asn
```

<210> SEQ ID NO 4
<211> LENGTH: 251
<212> TYPE: PRT
<213> ORGANISM: Salmonella enterica

<400> SEQUENCE: 4

```
Met Asp His Ala Ile Tyr Thr Ala Met Gly Ala Ala Ser Gln Thr Leu
1               5                   10                  15

Asn Gln Gln Ala Val Thr Ala Ser Asn Leu Ala Asn Ala Ser Thr Pro
            20                  25                  30

Gly Phe Arg Ala Gln Leu Asn Ala Leu Arg Ala Val Pro Val Asp Gly
        35                  40                  45

Leu Ser Leu Ala Thr Arg Thr Leu Val Thr Ala Ser Thr Pro Gly Ala
    50                  55                  60

Asp Met Thr Pro Gly Gln Leu Asp Tyr Thr Ser Arg Pro Leu Asp Val
65                  70                  75                  80

Ala Leu Gln Gln Asp Gly Trp Leu Val Val Gln Ala Ala Asp Gly Ala
                85                  90                  95

Glu Gly Tyr Thr Arg Asn Gly Asn Ile Gln Val Gly Pro Thr Gly Gln
            100                 105                 110

Leu Thr Ile Gln Gly His Pro Val Ile Gly Glu Gly Pro Ile Thr
        115                 120                 125

Val Pro Glu Gly Ser Ile Thr Ile Ala Ala Asp Gly Thr Ile Ser
    130                 135                 140

Ala Leu Asn Pro Gly Asp Pro Asn Thr Val Ala Pro Val Gly Arg
145                 150                 155                 160

Leu Lys Leu Val Lys Ala Glu Gly Asn Glu Val Gln Arg Ser Asp Asp
                165                 170                 175

Gly Leu Phe Arg Leu Thr Ala Glu Ala Gln Ala Glu Arg Gly Ala Val
            180                 185                 190

Leu Ala Ala Asp Pro Ser Ile Arg Ile Met Ser Gly Val Leu Glu Gly
        195                 200                 205

Ser Asn Val Lys Pro Val Glu Ala Met Thr Asp Met Ile Ala Asn Ala
    210                 215                 220

Arg Arg Phe Glu Met Gln Met Lys Val Ile Thr Ser Val Asp Glu Asn
225                 230                 235                 240

Glu Gly Arg Ala Asn Gln Leu Leu Ser Met Ser
                245                 250
```

<210> SEQ ID NO 5
<211> LENGTH: 99
<212> TYPE: DNA
<213> ORGANISM: Phaeodactylum tricornutum

<400> SEQUENCE: 5
atgatgttca tgagaattgc cgtagcagca ctggccttgc tggctgctcc ctccattcgt    60
gccgaagagg ctggtgaaga ggccaagatg ggtaccgtg                          99

<210> SEQ ID NO 6
<211> LENGTH: 67
<212> TYPE: DNA
<213> ORGANISM: Phaeodactylum tricornutum

<400> SEQUENCE: 6
atgtcgattc gtctcttctc taccgcctta ctagctgctt gcttagcaaa ggcaactgcc    60
caaactg                                                              67

<210> SEQ ID NO 7
<211> LENGTH: 1023
<212> TYPE: DNA
<213> ORGANISM: Artificial
<220> FEATURE:
<223> OTHER INFORMATION: polynucleotide

<400> SEQUENCE: 7

```
ggtaccgtcc gtaagggaga caagaagctc gctaaacccg ccaccaccaa agctgccaat      60
ccccagccgc gtcgccgtgc caacaaccgt cgtcgttcca accgcaccga tgctccggtc     120
tccaaagcct ccaccgtcac cggtttcgga cgcggaacga atgatgtcca cctctccggc     180
atgtcccgta tttcccaagc tgtcctcccg gctggaacgg gcacggatgg ctacgttgtg     240
gttgatgcca ccattgtccc cgacctcttg ccccgtctcg acacgctgcc cgcatttttc     300
cagcgttacg ccgtcgaaac gctcgagttc gaaattcagc ccatgtgccc cgctaacacc     360
ggcggaggtt acgtcgctgg attcctcccc gatcccaccg ataatgacca caccttcgat     420
gctttgcagg ccacccgtgg cgccgtggtc gccaagtggt gggaatcccg taccgtccgt     480
ccgcagtaca cgcgtacctt gctctggacc tcctccggaa aggaacagcg tctcacctcc     540
cccggacgtt tgattctctt gtgcgttggc aacaacaccg acgttgtcaa cgtttccgtc     600
ctctgccgtt ggtccgttcg tctctccgtc ccgtccctcg aaaccccccga agaaccacc    660
gctcccatta tgacgcaagg cccctctac aacgattcct tgtccacgaa cgattttaag      720
tccatcctct gggatccac cccctcgac attgccccg acggtgccgt gttccagttg        780
gaccgcccgt tgtccatcga ttactccctc ggaaccggag acgtcgaccg tgccgtctac    840
tggcatctca agaagttcgc cggtaataccc ggaacgcccg ctggttggtt tcgttgggga   900
atttgggaca acttcaacaa gacctttacc gacggagtcg cctactactc cgacgaacaa    960
ccccgccaaa ttttgctccc ggtgggtacg gtctgcaccc gcgtggactc cgaaaactct   1020
aga                                                                  1023
```

<210> SEQ ID NO 8
<211> LENGTH: 759
<212> TYPE: DNA
<213> ORGANISM: Artificial
<220> FEATURE:
<223> OTHER INFORMATION: polynucleotide

<400> SEQUENCE: 8

```
ggtaccgacc acgccatcta caccgccatg ggagccgctt cccagacgct caaccagcag      60
gctgtcaccg cctccaatct cgccaatgct tccaccccgg gattccgtgc ccagctcaac     120
gccctccgtg ctgttcccgt cgatggtctc tccctcgcta cccgtaccct cgtcacggcc     180
tccacgccgg gtgccgacat gaccccccgga cagctcgact cacctcccg tcccctcgat     240
gtcgctttgc agcaggacgg atggctcgtg tccaggctg ccgacggagc tgaaggatac      300
acgcgtaacg gaaacatcca ggtcggaccc accggacaac tcaccattca gggacacccc    360
attggagagg gaggacccat tacggtgccc gaaggctccg aaattaccat tgccgccgat    420
ggaaccatt ccgccctcaa cccgggagac cccccaaca ccgtggctcc cgtgggacgt      480
ctcaagctcg tgaaggccga gggaaacgaa gtccagcgtt ccgacgacgg actcttccgt     540
ttgaccgccg aagcccaggc cgaacgtgga gccgtcttgg ccgctgaccc ctccatccgc    600
attatgtccg gagtcctcga aggatccaac gtgaagccgg tcgaagctat gacggacatg    660
```

```
atcgctaacg cccgtcgctt cgagatgcag atgaaggtca ttacctccgt tgatgaaaat    720
gagggacgtg ccaaccagtt gctctccatg tcctctaga                           759
```

<210> SEQ ID NO 9
<211> LENGTH: 30
<212> TYPE: PRT
<213> ORGANISM: Phaeodactylum tricornutum

<400> SEQUENCE: 9

```
Met Ser Ile Arg Leu Phe Ser Thr Ala Leu Leu Ala Ala Cys Leu Ala
1               5                   10                  15

Lys Ala Thr Ala Gln Thr Cys Pro Thr Leu Ile Trp Ser Asp
            20                  25                  30
```

<210> SEQ ID NO 10
<211> LENGTH: 90
<212> TYPE: DNA
<213> ORGANISM: Phaeodactylum tricornutum

<400> SEQUENCE: 10

```
atgtcgattc gtctcttctc taccgcctta ctagctgctt gcttagcaaa ggcaactgcc    60
caaacttgcc ccactcttat ctggagtgac                                     90
```

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

```
Ala Ala Val Leu Leu Pro Val Leu Leu Ala Ala Pro
1               5                   10
```

<210> SEQ ID NO 12
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 12

```
gccgccgtcc tcctccccgt cttgttggct gccccc                              36
```

<210> SEQ ID NO 13
<211> LENGTH: 30
<212> TYPE: PRT
<213> ORGANISM: Artificial Sequence
<220> FEATURE:
<223> OTHER INFORMATION: Synthetic peptide

<400> SEQUENCE: 13

```
Tyr Pro Tyr Asp Val Pro Asp Tyr Ala Gly Tyr Pro Tyr Asp Val Pro
1               5                   10                  15

Asp Tyr Ala Gly Ser Tyr Pro Tyr Asp Val Pro Asp Tyr Ala
            20                  25                  30
```

<210> SEQ ID NO 14
<211> LENGTH: 90
<212> TYPE: DNA
<213> ORGANISM: Artificial Sequence
<220> FEATURE:
<223> OTHER INFORMATION: Synthetic polynucleotide

```
<400> SEQUENCE: 14
tacccgtacg acgtcccgga ctacgccgga taccoctacg atgttcccga ttacgctggt        60
tcctacccgt acgacgtgcc cgactacgct                                         90
```

ALGAL BASED EDIBLE VACCINES

The Sequence Listing submitted in text format (.txt) filed on Aug. 4, 2016, named "SequenceListing.txt", created on Aug. 4, 2016, 10.4 KB), is incorporated herein by reference.

FIELD OF THE INVENTION

The present invention relates in general to the field of edible vaccines. In particular, the present invention relates to vaccines comprising transgenic microalgae expressing a recombinant antigen that elicits an immune response towards a pathogen in an animal consuming the vaccine either directly or via an intervening organism.

BACKGROUND OF THE INVENTION

There is a global need for developing safe and effective vaccines for controlling diseases. Vaccines aim to evoke immune response leading to the production of antibodies (humoral immunity) or cell-mediated responses that will counter the particular disease. An ideal vaccine elicits an effective immunogenic response with a reasonable duration of immunity, has minimal adverse side effects, is economically feasible and is relatively simple to produce and use.

The vaccination field focuses on different types of vaccines and effective means of delivery. There are many types of vaccines, including inactivated, live attenuated, recombinant vaccines such as viral and bacterial vectors, toxoids, DNA vaccines and synthetic polypeptide combined vaccines. The vaccines can be delivered orally or parenterally. The parenteral administration of vaccines is inconvenient because of the risks involved and further because of the recipient's pain and fear. In addition, when the target organisms are aquatic animals or a large number of land animals, parenteral administration is practically impossible.

Aquaculture is a constantly growing food producing sector. Disease prevention is a key issue to maintain a sustainable development of aquaculture. Optimal husbandry and general management practices including biosecurity (protection from infectious agent), nutrition, genetics, system management and water quality are critical for maximizing aquatic animal health. However, all facilities are vulnerable to disease outbreaks because many pathogenic organisms are opportunistic and present in the environment. In addition, when species are reared at high densities, agents of infectious disease are easily transmitted between individuals. Treatments hitherto mainly include administering antibiotics and vaccines. Consumer health, food safety issues and concerns regarding the development of resistant bacteria reduce the use of antibiotics in aquaculture. Moreover, viral diseases cannot be treated with available antibiotics. The development of additional fish vaccines and effective means of delivery will lead to significantly decreased use of antibiotics in aquacultures.

*Streptococcus iniae* is a species of Gram-positive bacterium that is a leading fish pathogen in aquaculture operations worldwide. It infects a variety of cultured and wild fish which results in severe economic loss. Control of *Streptococcus iniae* by vaccination has met with limited success, thus antibiotic usage is the main current practice for reducing mortality and consequent economic loss.

U.S. Pat. No. 6,379,677 discloses polyvalent vaccines against *Streptococcus iniae* prepared from formalin-killed cells and concentrated extracellular products of *Streptococcus iniae*.

*Streptococcus agalactiae* is another important pathogen that affects aquatic species as well as animals and humans. It has been found worldwide in a variety of fish species, especially those living in warm water. For example, it was found in ya-fish (*Schizothorax prenanti*) farms in Sichuan Province, China (Geng Y. Transboundary and Emerging Diseases 59(4):369-375, 2012, Abstract). U.S. Pat. No. 7,204,993 discloses a composition comprising killed cells of isolated *Streptococcus agalactiae* as a vaccine for fish. The composition is suggested to be administrated by intraperitoneal or intramuscular injection, bath immersion, oral administration, or nasal administration.

The infectious salmon anemia (ISA) virus is of the family Orthomyxoviridae, genus Isavirus. ISA is a serious disease of farmed Atlantic salmon. ISA was first detected in Norway in 1984 and was characterized by severe anemia and circulatory disturbances. As with other viral vaccines for fish, commercially available vaccines against ISA, based upon inactivated whole virus, have questionable field effectiveness.

Viral nervous necrosis (VNN) is caused by nervous necrosis viruses (NNV) that are a major pathogen of several economically important fish species worldwide. The NNV are non-enveloped, small single-stranded sense RNA viruses. Betanodaviruses cause viral nervous necrosis (VNN) or viral encephalopathy and retinopathy (VER). More than 40 fish species, most of them marine, were reported to be susceptible to Betanodavirus (Nakai T. et al. The Israeli journal of aquaculture, 61(3):198-207 2009) Immunization using inactivated betanodavirus was suggested as an effective strategy to protect grouper larvae against VNN. Effective NNV vaccines must be administered at the early larval stage before infection with NNV has occurred. Due to the small size of larvae and their sensitivity to stress, an oral vaccination is a more suitable means of immunization than injection or immersion.

*Salmonella* infection is a major cause of gastroenteritis in humans worldwide and it is often associated with consumption of raw or uncooked poultry products. Eggs contaminated with *Salmonella enterica Serovar enteritidis* are associated with a significant number of human illnesses and continue to be a public health concern. A substantial reduction of the intestinal population of *Salmonella enterica Serovar enteritidis* is a desirable aim of vaccination. Live attenuated vaccines are widely used in the poultry industry, breeding and layers stock. Using this type of vaccines has some disadvantages, mainly because there is a small risk that attenuated forms of a pathogen can revert to a dangerous form, and, in addition, the pathogen may infect other animals. A vaccine not containing any live form of the pathogen which will stimulate the intestinal immune response can be of enormous advantage to the poultry industry.

There is a need for routes to administer vaccines to aquatic farm as well as terrestrial animals that are not costly and do not require laborious efforts. Oral administration of vaccines will be ideal for these purposes. Oral delivery of vaccines to humans is also desirable, as this mode of administration does not require professional manpower and prevents the discomfort involved in parenteral administration. For successful oral delivery, antigens should be protected from chemical and enzymatic degradation that may occur during processing the antigens into food or a feed composition and through the delivery via the animal or human gastrointestinal tract. In addition, the antigen should overcome structural barriers that preclude entry into the animal or access to the target destination.

Microalgae (single cell alga or phytoplankton) represent the largest, but most poorly understood, kingdom of microorganisms on the earth. Like plants are to terrestrial animals, the microalgae represent the natural nutritional base and primary source of all the phytonutrients in the aquatic food chain. The use of algae for vaccine production offers several advantages such as low cost, safety and easy scaling up.

Expression of recombinant proteins in algae has been reported, and various methods are available for production of exogenous proteins within the algae cells, particularly within the cell plastid. International (PCT) Application Publication No. WO 2011/063284 discloses methods of expressing therapeutic proteins in photosynthetic organisms, including prokaryotes such as cyanobacteria, and eukaryotes such as alga and plants. Transformation of eukaryotes is preferably into the plastid genome, typically into the chloroplast genome.

U.S. Pat. Nos. 7,410,637 and 8,282,915 disclose delivery systems and methods for delivering a biologically active protein to a host animal. The systems and methods provided include obtaining an algal cell transformed by an expression vector, the expression vector comprising a nucleotide sequence coding for the biologically active protein, operably linked to a promoter. In one illustrated embodiment, the biologically active protein is an antigenic epitope and upon administration to the animal the algal cell induces an immune response in the host animal.

International (PCT) Application Publication No. WO 2002/076391 discloses the use of microbial cells which are used as feed components in aquaculture or agriculture, and which also contain exogenous peptides, proteins, and/or antibodies, which will convey resistance or immunity to viral or bacterial pathogens or otherwise improve the health and performance of the species consuming said microbial cells. The microbial cells can be yeast, fungi, bacteria, or algae. The proteins and/or antibodies may be expressed inside the microbial cells by direct genetic modification of the microbe itself, or by the infection of the microbe with a virus that has been altered to express the protein of interest.

International (PCT) Application Publication No. WO 2008/027235 discloses methods for prevention, amelioration or treatment of a disease or disorder in an aquatic animal, by feeding the aquatic animal directly or indirectly with genetically modified microalgae that express a recombinant molecule that specifically targets one or more key epitopes of a pathogen that infects the aquatic animal.

U.S. Patent Application Publication No. 2011/0014708 discloses method of producing a foreign desired gene product in algae that comprises weakening or removing the algae cell wall by a protein enzyme solution to facilitate the gene transfer and a feed composition comprising the transgenic algae or its offspring. The invention also provides a modified nucleic acid for expressing bovine lactoferricin (LFB) in algae.

International (PCT) Application Publication No. WO 2014/030165 to the inventor of the present invention, published after the priority date of the present invention, discloses transgenic microalgae expressing exogenous biologically active proteins and use thereof for oral delivery of the biologically active proteins to animals and humans.

However, there is still an unmet need for and it would be highly advantageous to have an effective oral delivery system for vaccination that is easy for production and use, maintains the immunogenic activity of the antigen and facilitates absorption of the antigen by an organism.

SUMMARY OF THE INVENTION

The present invention provides algal based edible vaccines providing for effective immunity of the target organism to a pathogen. The present invention provides vaccines comprising transgenic microalgae expressing at least one exogenous antigen that is localized within a predetermined subcellular compartment in an immunogenic form. The antigen expressing microalgae are used as food or a food additive applicable for feeding aquatic and land animals, as well as humans. The edible vaccine is characterized by being immunogenically active, evoking at least one immune response resulting in increased resistance of the target organism to a pathogen. The target organism can consume the transgenic microalgae either directly or indirectly, via an intervening organism.

The present invention discloses that the expressed antigen remains active and exerts its immunogenic activity in animals that orally consume the transgenic algae or consume organisms fed with the transgenic microalgae. Typically, the antigen remains in its intact form. Unexpectedly, the antigen elicits an immunogenic response in the target organism also when the transgenic microalgae are consumed indirectly via an intervening organism. Without wishing to be bound by any particular theory or mechanism of action, the preserved immunogenic activity of the antigen may be attributed to its localization within the intact microalga, such that the microalgal cell serves as a natural encapsulation material protecting the antigen from being degraded in the animal's gastrointestinal tract and/or stomach. According to certain typical embodiments of the present invention, the antigen is localized in a microalgal subcellular compartment, particularly in the vacuole. The localization in the algal vacuole provides an additional protection from protease degradation and efficient transfer of the antigen from the intestine to the blood stream of the target animal in which the immunogenic response is elicited.

Thus, according to one aspect, the present invention provides an edible vaccine comprising transgenic eukaryotic microalga comprising an expression cassette comprising at least one polynucleotide encoding an exogenous antigen, wherein the encoded exogenous antigen is localized within a subcellular compartment of the microalga cell.

The subcellular compartment of the transgenic microalga in which the antigen is localized depends on the microalga species, the type of the antigen expressed and the animal species to be fed. According to certain embodiments, the subcellular compartment is selected from the group consisting of vacuole, endoplasmic reticulum, Golgi system, lysosome and peroxisome. Each possibility represents a separate embodiment of the present invention.

According to certain exemplary embodiments, the exogenous antigen is localized within the microalga cell vacuole. According to these embodiments, the expression cassette further comprises a polynucleotide encoding a vacuole targeting peptide. According to certain embodiments, the polynucleotide encodes a vacuolar targeting peptide having at least 80% homology, typically at least 90% homology, more typically at least 98% homology to the amino acid sequence set forth in any one of SEQ ID NO:1 and SEQ ID NO:9. According to certain embodiments, the polynucleotide encodes the amino acid sequence set forth in SEQ ID NO:1. According to certain exemplary embodiments, the polynucleotide encoding the vacuole targeting peptide has the nucleic acids sequence set forth in any one of SEQ ID NO:6 and SEQ ID NO:10. Each possibility represents a separate embodiment of the present invention.

According to certain other exemplary embodiments, the exogenous antigen is localized within the microalga cell endoplasmic reticulum (ER). According to these embodiments, the expression cassette further comprises a polynucleotide encoding an ER targeting peptide. According to certain embodiments, the polynucleotide encodes an ER targeting peptide having at least 80% homology, typically at least 90% homology, more typically at least 98% homology to a *Phaeodactylum tricornutum* endoplasmic reticulum (Bip) leader sequence. According to certain embodiments, the polynucleotide encodes the *Phaeodactylum tricornutum* endoplasmic reticulum (Bip) leader sequence having the amino acid sequence set forth in SEQ ID NO:2. According to certain exemplary embodiments, the polynucleotide encoding the ER targeting peptide has the nucleic acids sequence set forth in SEQ ID NO:5.

According to certain embodiments, the antigen induces an immune response in a target subject consuming the vaccine comprising the transgenic microalga against a disease caused by a pathogen.

According to certain embodiments, the vaccine comprises an intervening organism that ingested the transgenic microalgae. According to these embodiments, the antigen induces an immune response in a target subject consuming the vaccine comprising the intervening organism. According to certain exemplary embodiments, the intervening organism is fed with the microalgae. According to additional embodiments, the intervening organism is known to be used as a food source for the target animal subject. According to some embodiments the target animal is fish. According to certain exemplary embodiments, the fish is in its larva or post larva form. According to some embodiments, the intervening organism that ingested the transgenic microalgae is selected from the group consisting of *Artemia* and rotifer.

According to some embodiments, the induced immune response confers or increases resistance of the target subject to a pathogen.

According to certain embodiments, the target subject is selected from the group consisting of aquatic animals, land animals and humans.

According to certain exemplary embodiments, the target aquatic animal is a fish.

According to some embodiments, the expressed antigen vaccinates a fish consuming said vaccines against a disease caused by a pathogen. According to certain embodiments, the pathogen is selected from the group consisting of *Streptococcus iniae, Streptococcus agalactiae*, Betanodavirus and infectious salmon anemia virus. Each possibility represents a separate embodiment of the invention.

According to some exemplary embodiments, the antigen is a capsid protein of the Betanodavirus genus (nervous necrosis viruses, NNV) or a fragment thereof. According to additional embodiments, the polynucleotide of the invention encodes an amino acid sequence comprising at least 80% homology, typically at least 90% homology, more typically at least 98% homology to a sequence of nervous necrosis viruses (NNV) capsid protein. According to certain exemplary embodiments, the NNV capsid protein has the amino acid sequence set forth in SEQ ID NO:3. According to certain exemplary embodiments, the polynucleotide encoding the NNV capsid protein comprises the nucleic acids sequence set forth in SEQ ID NO:7.

According to some embodiments, the expressed antigen vaccinates poultry consuming said vaccines against a disease caused by a pathogen. According to other certain embodiments, the pathogen is *Salmonella enterica*.

According to yet additional embodiments, the expressed antigen vaccinates a human subject consuming said vaccines against a disease caused by a pathogen. According to certain embodiments, the pathogen is selected from the group consisting of *salmonella* enteric and *Streptococcus agalactiae*.

According to other exemplary embodiments, the antigen is a flagellin protein or a fragment thereof. In additional embodiments, the flagellin is of *Salmonella enterica* serovar *enteritidis*. According to certain embodiments, the polynucleotide of the invention encodes an amino acid sequence comprising at least 80% homology, typically at least 90% homology, more typically at least 98% homology to a sequence of *Salmonella enterica Serovar enteritidis* flagellin According to exemplary embodiments, the flagellin has the amino acid sequence set forth in SEQ ID NO:4. According to certain exemplary embodiments, the polynucleotide encoding flagellin comprises the nucleic acid sequence set forth in SEQ ID NO:8.

Various microalgae species can be used according to the teachings of the present invention. According to certain embodiments, the microalga used according to the teachings of the present invention is a marine microalga. According to certain embodiments, the microalga is selected from the group consisting of, but not restricted to, *Phaeodactylum tricornutum; Dunaliella* spp.; *Nannochloropsis* spp. including *Nannochloropsis oculata, Nannochloropsis salina, Nannochloropsis gaditana; Nannochloris* spp., *Tetraselmis* spp. Including *Tetraselmis suecica, Tetraselmis chuii; Isochrysis galbana; Pavlova* spp.; *Amphiprora hyaline; Chaetoceros muelleri*; and *Neochloris oleoabundans*. Each possibility represents a separate embodiment of the present invention.

According to certain specific embodiments, the microalga is selected from the group consisting of *Phaeodactylum tricornutum, Nannochloris* spp., *Nannochloropsis* spp. and *Dunaliella* spp.

According to other specific embodiments, the microalga is *Phaeodactylum tricornutum*.

The transgenic microalgae of the present invention can be transformed to express any antigen evoking an immunogenic response in the target subject consuming same.

According to certain embodiments, the molecular weight of the expressed antigen is up to 100 kDa. According to other embodiments, the molecular weight of the expressed antigen is up to 90 kDa, 80 kDa, 70 kDa or 60 kDa. According to other embodiments, the molecular weight of the expressed antigen is in the range of 1-50 kDa.

According to additional embodiment, the present invention provides an edible composition comprising the vaccines of the present invention. According to some embodiments, the edible composition is an animal food composition. According to exemplary embodiments, the animal food composition is for feeding aquatic animals. According to some embodiments, the animal food composition is for feeding land farm animals According to other embodiments, the animal food composition is for feeding poultry. As described hereinabove, the edible composition is used for oral delivery of vaccines.

According to an additional aspect, the present invention provides a method for oral delivery of an antigen to a subject in need thereof, the method comprising orally administering to the subject an effective amount of a vaccine comprising a transgenic eukaryotic microalga comprising an expression cassette comprising at least one polynucleotide encoding an exogenous antigen, wherein the encoded exogenous antigen is localized within a subcellular compartment of the microalga cell. According to certain embodiments, the subcellular compartment is selected from the group consisting of vacuole, endoplasmic reticulum, Golgi system, lysosome and peroxisome. Each possibility represents a separate embodiment of the present invention.

According to certain specific embodiments, the encoded exogenous antigen is localized within the microalga cell vacuole. According to other specific embodiments, the exogenous antigen is localized within the microalga cell endoplasmic reticulum.

According to certain embodiments, the vaccine is administered within a food composition. The composition is any of the food compositions as described hereinabove.

The microalga is any of the microalgae as described hereinabove.

According to certain embodiments, the exogenous antigen elicits an immune response in a subject consuming the vaccine. According to some embodiments, the exogenous antigen vaccinates the subject against diseases caused by a pathogen.

According to certain embodiments, the subject is selected from the group consisting of aquatic animals, land animals and humans. Each possibility represents a separate embodiment of the present invention. According to some embodiments, the subject is a fish.

According to certain embodiments, the animal subject is an aquatic or land animal. The land animal may optionally be any animal grown for food or for a non-food purpose (the latter including but not limited to work animals, pets and the like), including but not limited to cows, pigs, horses, dogs, cats, mice, rats, rabbits, guinea pigs, poultry and the like. The aquatic animal may optionally be any animal grown for food or for a non-food purpose (the latter including but not limited to ornamental, and the like).

According to an additional aspect, the present invention provides a method for oral delivery of an antigen to an animal subject, the method comprising the steps of:

(a) orally administering to an intervening organism an effective amount of transgenic microalga comprising an expression cassette comprising at least one polynucleotide encoding an exogenous antigen, wherein the encoded exogenous antigen is localized within a subcellular compartment of the microalga cell, thereby obtaining an intervening organism that have ingested the transgenic microalga; and (b) orally administering to the animal subject an effective amount of the intervening organism that has ingested the transgenic microalga.

According to certain embodiments, the animal subject is selected from the group consisting of aquatic animals and land animals Each possibility represents a separate embodiment of the present invention.

According to certain embodiments, the antigen evokes an immunogenic response in the subject, the immunogenic response being effective against diseases caused by a pathogen.

According to some embodiments, the subject is a fish. According to certain embodiments, the intervening organism is selected from the group consisting of *Artemia* and rotifer.

Other objects, features and advantages of the present invention will become clear from the following description and drawing.

BRIEF DESCRIPTION OF THE DRAWING

FIG. 2 demonstrates that vacuole targeted proteins expressed in algae are delivered to *Artemia* consuming the algae in their intact size. *Artemia* were fed with WT or with vacuole targeted—GFP expressing algae (FIG. 2A) or with two algae lines each expressing vacuole targeted—fish growth hormone tagged with hemagglutinin epitope tag (HA) (FIG. 2B; A and B) for several hours as indicated. *Artemia* were then washed and total protein was extracted, loaded on SDS-PAGE and subjected to Western blot analysis. Membranes were reacted with either anti GFP (FIG. 2A) or with anti HA antibody (FIG. 2B).

FIG. 3 shows that vacuole-targeted GFP expressed in algae is delivered to *Artemia* in its functional form. *Artemia* were fed with WT (FIG. 3A) or with GFP (FIG. 3B) expressing algae and then analyzed for GFP fluorescence under fluorescent binocular 4 h post feeding.

DETAILED DESCRIPTION OF THE INVENTION

The present invention provides compositions and methods for oral delivery of vaccines to an organism in need thereof. In particular, the present invention provides transgenic microalgae expressing an antigen and edible compositions comprising same. The present invention discloses that the antigen can be transformed from the microalgae into the subject consuming same, either directly or via an intervening organism and furthermore, to maintain its activity and evoke an immunogenic response in cells or tissues of said subject. According to certain typical embodiments of the present invention, the antigen is localized in a microalgal subcellular compartment, particularly in the vacuole.

Most of the vaccines against the animal diseases mentioned hereinabove and used worldwide are whole-organism vaccines, either live and attenuated or killed forms. However, there is a small risk that attenuated forms of a pathogen can revert to a dangerous form, and may still be able to cause disease in immunocompromised vaccine recipients (such as those with AIDS) and leak to the environment as well. This risk does not exist when the vaccine is based on a single antigen or several specific antigen epitopes, as utilized according to the principles of the present invention. Additionally the chances of adverse reactions to these types of vaccines are lower.

DEFINITIONS

The terms "microalga" or "microalgae" are used herein in their broadest scope and refer to unicellular microscopic eukaryotic algae, typically found in freshwater and marine systems. Depending on the species, the microalgae size can range from a few micrometers (μm) to a few hundreds of micrometers. According to certain currently specific embodiments, the term refers to marine eukaryotic microalga or microalgae.

The term "vaccine" refers to an immunogenic composition that improves immunity or induces immunity in a subject to a particular disease. A vaccine typically contains an immunogenic agent that resembles or constitutes at least one component (an antigen) of a disease-causing organism. The agent stimulates the immune system so that it can more easily identify the corresponding pathogen that it later encounters. The immune response or defense response elicited by the antigen is protective in the host animal in the sense that a subsequent infection of the host animal by the pathogenic organism from which the antigen is derived would be prevented, would not cause a disease or, if a disease was caused, the disease or symptoms associated with the disease would be ameliorated. Preferably, the antigen itself does not cause disease or any other adverse symptoms in the target animal Advantageously, the vaccines of the present invention comprise an exogenous antigen within a subcellular compartment of a transgenic microalga.

The term "immunogenicity" or "immunogenic" relates to the ability of a substance to stimulate or elicit an immune response. Immunogenicity is measured, for example, by determining the presence of antibodies specific for the substance. The presence of antibodies is detected by methods known in the art, for example using an ELISA assay.

The term "antigen" as is used herein refers to an agent that is the target of the immunogenic response system of a host animal and is capable of eliciting an immune response or defense response in the host animal According to the present invention the antigen is a protein or a peptide. According to certain embodiments, the protein or peptide acquires additional modifications. According to certain embodiments of the invention, the antigen is at least partially derived from a pathogenic microorganism selected from the group consisting of bacterium, virus, fungus, or parasite (e.g., protozoan or helminth). According to additional embodiments, the antigen is at least partially derived from a prion.

The term "peptide" as used herein refers to a polymer of amino acid residues. By "peptide" it is meant an amino acid sequence consisting of 2 to 50 amino acids. By "protein" it is meant an amino acid sequence consisting of 50 or more amino acid residues. The terms peptide and protein are used interchangeable throughout the specification.

The terms "polynucleotide", "polynucleotide sequence" and "nucleic acid sequence" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids. According to certain currently exemplary embodiments, the polynucleotides of the present invention are designed based on the amino acid sequence of the protein of interest employing a codon usage of the particular microalga species to be transformed.

The terms "expression cassette" and "construct" or "DNA construct" are used herein interchangeably and refer to an artificially assembled or isolated nucleic acid molecule which includes the polynucleotide encoding the protein of interest and is assembled such that the protein is expressed. The construct may further include a marker gene which in some cases can also encode a protein of interest. According to certain embodiments of the present invention, the protein of interest is an antigen operably linked to a subcellular localization peptide. The expression cassette further comprising appropriate regulatory sequences operably linked to the polynucleotide encoding the protein of interest. It should be appreciated that the inclusion of regulatory sequences in a construct is optional, for example, such sequences may not be required in situations where the regulatory sequences of a host cell are to be used.

According to certain embodiments, the microalga comprises an expression cassette comprising operably linked elements including a promoter sequence, a polynucleotide encoding the antigen and vacuole targeting sequence, and a termination sequence.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The terms "promoter element", "promoter", or "promoter sequence" as used herein, refer to a DNA sequence that is located upstream to the 5' end (i.e. precedes) the protein coding region of a DNA polymer. The location of most promoters known in nature precedes the transcribed region. The promoter functions as a switch, activating the expression of a gene or part thereof. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoters may be derived in their entirety from a native gene, or be composed of different elements derived from different promoters found in nature, or even comprise synthetic DNA segments. It is understood by those skilled in the art that different promoters may direct the expression of a gene or part thereof in different tissues or cell types, at different stages of development, and/or in response to different environmental conditions. It is further recognized that since in most cases the exact boundaries of regulatory sequences have not been completely defined, DNA fragments of some variation may have identical promoter activity. Promoters which cause a gene to be expressed in most cell types at most times are commonly referred to as "constitutive promoters".

According to some embodiments, the promoter is the organism's native promoter or a heterologous promoter. According to additional embodiments, the promoter is a constitutive promoter or induced promoter.

Any promoter known in the art to be active in microalgae can be used according to the teachings of the present invention. Non-limiting examples are fucoxanthin chlorophyll protein A (fcpA); B (fcpB); C (fcpC) and E (fcpE) promoters as well as any light harvesting complex (Lhc) promoter. Non-light harvesting related promoters can also be used, including, but not limited to, the nopaline synthase promoter; poly-adenylation sequences from the Ti plasmid of *Agrobacterium tumefaciens*; the promoter region of the tubB2; the PL promoter from bacteriophage λ; the promoter of the cytomegalovirus (PCMV); the Rous sarcoma virus long terminal repeat (PRSV-LTR) promoter; the cauliflower mosaic virus 35s (PCaMV35s) promoter; the bacterial tφ promoter; the heat shock protein 70A promoter (HSP70A); the $CO_2$ responsive promoter sequence of the chloroplastic carbonic anhydrase (Pptca1) and a promoter of Rubisco small subunit 2 (RBCS2).

As used herein, the term "food" refers to food for animal consumption, including land and aquatic animals.

The term "aquaculture" as used herein, refers to aquatic organism cultivated under controlled conditions. An "aquatic organism" or "aquatic animal" are used herein interchangeably and refer to an organism grown in water, either fresh- or marine water. The aquatic organisms include, but are not limited to, fish, e.g., tilapia, sea bass, grouper, salmon, striped bass, catfish, sea bream, rainbow trout, barramundi, red drum, goldfish, koi fish, angel fish and carp. The term "fish" includes all stages of the fish development, including larva and post larva forms.

The teachings of the present invention are illustrated below with regard to animals, particularly animals grown in aquaculture and model land animals as non-limiting examples for implementation of at least some aspects of the present invention.

Currently available aquaculture systems are generally classified as open or closed. Open systems are typically created by building a net-pen in a body of water, such as a lake or stream. Closed systems generally re-circulate the water in a closed tank, the water being pumped from the tank through a treatment cycle and back into the tank.

Aquaculture systems are used to grow aquatic animals such as fish, crustaceans and mollusks, to a size where they are marketable for different uses, primarily as food products but also as ornamentals. According to some embodiments, the present invention provides improved vaccines for fish or other aquatic animals.

Oral administration of an edible composition comprising antigens is of significant economic value in aquaculture as well as in agriculture, eliminating the need to administer a composition comprising to each animal individually.

According to another aspect, the present invention provides a transgenic eukaryotic microalga comprising an expression cassette comprising at least one transcribable polynucleotide encoding an exogenous antigen, wherein the expressed exogenous antigen is localized within a subcellular compartment of the microalga cell.

Various algae species can be used according to the teachings of the present invention. According to certain embodiments, the alga is marine microalga. An exemplary list of marine microalga that can be used according to the teachings of the present invention includes, but is not limited to, *Phaeodactylum tricornutum; Dunaliella* spp.; *Nannochloropsis* spp. including *Nannochloropsis oculata, Nannochloropsis salina, Nannochloropsis gaditana; Nannochloris* spp., *Tetraselmis* spp. including *Tetraselmis suecica, Tetraselmis chuii; Isochrysis galbana; Pavlova* spp.; *Amphiprora hyaline; Chaetoceros muelleri*; and *Neochloris oleoabundans*. The algae come from and represent a large taxonomical cross section of species (Table 1).

used as a food source for animals, especially fish and marine invertebrates but also for land animals *Phaeodactylum tricornutum* is a marine alga and therefore is grown in marine media which is much less susceptible to pathogenic infections, in contrast to fresh water grown microalgae like *Chlamydomonas. Phaeodactylum tricornutum* known for its ability to accumulate high levels of eicosapentaenoic acid (EPA) which is a highly important omega-3 polyunsaturated fatty acid (PUFA) (Patil et. al., Aquacult Int., 2007, 15:1-9). In a study, which was carried out to evaluate three microalgae as potential nutrient sources in diets for monogastric animals, it was concluded that among the investigated algae, *Phaeodactylum tricornutum* was the preferable source of digestible nutrients (Skrede A. et al., J of Animal and Feed Sci., 2011, 20:131-142). Thus, vaccines comprising transgenic *Phaeodactylum tricornutum* according to the teachings of the present invention are highly adequate for oral administration.

The primary use of the transgenic microalgae of the present invention is as a vaccine vehicle composed as an edible composition. The exogenous antigen expressed in the algal cell should reach the target cell or tissue of the subject consuming the composition in its immunogenic form, wherein the subject is aquatic or land animal. One of the principal obstacles in oral delivery of antigens is the susceptibility of the antigen to the environmental conditions throughout the process of preparing the oral delivery product and its storage and thereafter within the body of the target subject in the gastrointestinal tract.

The present invention now discloses that the exogenous antigen localized within a subcellular compartment of the microalga preserves its immunogenic activity when consumed by aquatic as well as by terrestrial animals. Without wishing to be bound by any specific theory or mechanism of action, the antigen activity may be preserved by the intact alga cell, particularly by the cell walls, which may act as a form of encapsulation that protect the antigen from the outside harsh environment throughout the growth and processing of the algal biomass and furthermore from the environment of the gastrointestinal tract of the subject animal consuming the algae. Furthermore, the present invention discloses that the exogenous antigen preserves its immunogenic activity when delivered via an intervening

TABLE 1

Phylogeny of some of the eukaryotic algae

| Genus | Family | Order | Phylum | Kingdom |
|---|---|---|---|---|
| *Phaeodactylum* | Phaeodactylaceae | Naviculales | Bacillariophyta | Chromalveolata |
| *Dunaliella* | Dunaliellaceae | Chlamydomonadales | Chlorophyta | Viridaeplantae |
| *Nannochloris* | Coccomyxaceae | Chlorococcales | Chlorophyta | Viridaeplantae |
| *Tetraselmis* | Chlorodendraceae | Chlorodendrales | Chlorophyta | Viridaeplantae |
| *Nannochloropsis* | Monodopsidaceae | Eustigmatales | Heterokontophyta | Chromobiota |
| *Pavlova* | Pavlovaceae | Pavlovales | Haptophyta | Chromobiota |
| *Isochrysis* | Isochrysidaceae | Isochrysidales | Haptophyta | Chromobiota |

Phylogeny according to Guiry, M D and Guiry G M. 2013. AlgaeBase. World-wide electronic publication, National University of Ireland, Galway.

According to certain specific embodiments, the transgenic microalga used according to the teachings of the present invention is *Phaeodactylum tricornutum*. The alga *Phaeodactylum tricornutum* is a diatomaceous unicellular alga that forms part of phytoplankton and originates from temperate climes. This alga is readily amenable to transformation and the transformed alga growth well in aquaculture. In addition, this alga is nontoxic and nonpathogenic, and can be organism that is first fed with the transgenic microalgae and then serve as a food for the target animal.

Various exogenous antigens can be used according to the invention. The antigens are used to elicit an immune response in the organisms that consume the microalgae according to the invention or organisms that fed with those organisms that consume the microalgae (intervening organisms).

According to some exemplary embodiments, the target organism is fish and the antigen is a nervous necrosis viruses (NNV) capsid protein or a fragment thereof. According to additional embodiments, the polynucleotide of the invention encodes an amino acid sequence comprising at least 80% homology, typically at least 90% homology, more typically at least 98% homology to a sequence of nervous necrosis viruses (NNV) capsid protein. According to certain exemplary embodiments, the NNV capsid protein has the amino acid sequence set forth in SEQ ID NO:3. According to certain exemplary embodiments, the polynucleotide encoding the NNV capsid protein comprises the nucleic acids sequence set forth in SEQ ID NO:7. Fish vaccination with microalgae expressing the NNV capsid protein confers viral resistance in said fish. The NNV capsid protein is expressed in the microalgae and localized to its vacuole. Without wishing to be bound by any specific theory or mechanism of action, it is stipulated that the vacuolar storage of the NNV protein protects it from being degraded by the fish digestion system and facilitates its delivery to the fish as to elicit the immune response.

According to other exemplary embodiments, the antigen is a flagellin protein or a fragment thereof. In additional embodiments, the flagellin is of *Salmonella enterica* serovar *enteritidis*. According to certain embodiments, the polynucleotide of the invention encodes an amino acid sequence comprising at least 80% homology, typically at least 90% homology, more typically at least 98% homology to a sequence of *Salmonella enterica Serovar enteritidis* flagellin According to exemplary embodiments, the flagellin has the amino acid sequence set forth in SEQ ID NO:4. According to certain exemplary embodiments, the polynucleotide encoding flagellin comprises the nucleic acid sequence set forth in SEQ ID NO:8. According to certain embodiments, the vaccination of poultry with microalgae expressing the flagellin protein confers resistance to *salmonella* in said poultry.

According to certain embodiments, the subcellular compartment is selected from the group consisting of vacuole, endoplasmic reticulum, Golgi system, lysosome and peroxisome. Each possibility represents a separate embodiment of the present invention. According to certain currently specific embodiments, the exogenous antigen is localized within the microalga cell vacuole.

Another problem to be solved in oral delivery of vaccines is the penetration of antigens through the gastrointestinal epithelial cell membranes of the target animal subject that strictly limits their penetration. A minimum level of lipophilicity is needed for the antigens to partition into epithelial cell membranes for transcellular absorption. Unexpectedly, the present invention discloses that targeting the antigen within the microalgae vacuole lead to efficient absorption of the expressed antigen from the gastro intestinal track into the blood stream of the animal consuming the transgenic microalgae. Vacuoles are part of the endomembrane system of a cell; therefore, without wishing to be limited by a single hypothesis or mechanism of action, targeting antigens to the microalga cell vacuole, which is part of the endomembrane system, may increase absorption through the gastrointestinal tract of the animal once the alga is consumed and its walls are degraded by the animal subject. Such an increase in absorption may be due to increasing the "perceived" lipophilicity of antigen molecules by the epithelial cell membranes, resulting in efficient absorption through the intestine. In addition, it is also possible that providing the antigen through the vacuole increases storage stability of the antigen. Various combinations of the above may also play a role. In any case, targeting the antigen to the vacuole clearly increases the functional efficacy of orally administered vaccines.

Additionally, exogenous antigen expressed by the microalgae can be so designed to enhance its uptake by the epithelial cell membranes of the animal subject consuming the transgenic algae. According to some embodiments, the expression cassette of the present invention further comprises a polynucleotide encoding a protein domain that enhances the uptake of the expressed exogenous antigen by a xenogeneic cell or tissue.

The particular uptake enhancing domain is selected according to the type of the xenogeneic cell, which depends on the species of the subject animal consuming the transgenic microalgae. According to certain embodiments, the expression cassette further comprises a polynucleotide encoding a cell penetrating peptide (CPP). According to some embodiments, the CPP is selected from the group consisting of, but not limited to, the trans-activating transcriptional activator (TAT) from Human Immunodeficiency virus 1 synthesized according to the *Phaeodactylum tricornutum* codon usage or part thereof; and the membrane translocating sequence (MTS) of a fibroblast growth factor synthesized according to the *Phaeodactylum tricornutum* codon usage or part thereof. Each possibility represents a separate embodiment of the present invention.

Any method for transforming microalgae as is known in the art can be used according to the teachings of the present invention. Transformation methods include particle bombardment, electroporation, microporation, vortexing cells in the presence of exogenous DNA, acid washed beads and polyethylene glycol-mediated transformation. Methods and tools for transformation of eukaryotic algae can be found, for example, in International (PCT) Application Publication No. WO 1997/039106.

Typically, to prepare vectors for making the transgenic algae, the polynucleotide encoding the exogenous antigen is first cloned into an expression vector, a plasmid that can integrate into the algal genome. In such an expression vector, the DNA sequence which encodes the exogenous antigen is operatively linked to an expression control sequence, i.e., a promoter, which directs mRNA synthesis. As described hereinabove, the promoter can be an endogenous promoter, i.e., a promoter that directs transcription of genes that are normally present in the algae. According to certain embodiments, the vector further comprises a polynucleotide encoding a resistance gene to enable selection of transformed algae. According to certain currently exemplary embodiments, the vector comprises a polynucleotide encoding a protein conferring resistance to zeocine and phleomycin.

Culturing conditions of the transformed algae depend on the alga species used, as is known to the skilled artisan and as exemplified hereinbelow. Typically, the algae are grown under conditions that enable photosynthesis. Since photosynthesis requires sunlight and $CO_2$ and the microalgae further require either fresh, brackish or marine water mixed with the appropriate fertilizers to grow, microalgae can be cultivated in, for example, open ponds and lakes. However, the open systems are more vulnerable to contamination than a closed system, and furthermore, genetically modified microalgae grown in open aqueous reservoirs may be taken as hazardous to the environments. In addition, in open systems there is less control over water temperature, $CO_2$ concentration, and lighting conditions. The growing season is largely dependent on location and, aside from tropical areas, is limited to the warmer months of the year. An open system, however, is cheaper to set up and/or maintain than a closed system.

Another approach to growing the microalgae is thus to use a semi-closed system, such as covering the pond or pool with a structure, for example, a "greenhouse-type" structure. While this can result in a smaller system, it addresses many of the problems associated with an open system. The advantages of a semi-closed system are that it can allow for the desired microalgae to be dominant over an invading organism by allowing the microalgae of interest to out-compete the invading organism for nutrients required for its growth, and it can extend the growing season. For example, if the system is heated or cooled, the microalgae can grow year round.

Alternatively, the microalgae can be grown in closed structures such as photobioreactors, where the environment is under stricter control compared to open systems or semiclosed systems. A photobioreactor is a bioreactor which incorporates some type of light source to provide photonic energy input into the reactor. The term photobioreactor can refer to a system closed to the environment and having no direct exchange of gases and contaminants with the environment. A photobioreactor can be described as an enclosed, illuminated culture vessel designed for controlled biomass production of phototrophic liquid cell suspension cultures. Examples of photobioreactors include, for example, glass containers, plastic/glass tubes, tanks, plastic sleeves, and bags. Examples of light sources that can be used to provide the energy required to sustain photosynthesis include, for example, fluorescent bulbs, LEDs, and natural sunlight. Because these systems are closed everything that the organism needs to grow (for example, carbon dioxide, nutrients, water, and light) must be introduced into the bioreactor. Photobioreactors, despite the costs to set up and maintain them, have several advantages over open systems, they can, for example, prevent or minimize contamination, offer better control over the culture conditions (for example, pH, light, carbon dioxide, and temperature), prevent water evaporation, lower carbon dioxide losses due to degassing, and permit higher cell concentrations. On the other hand, certain requirements of photobioreactors, such as cooling, mixing, control of oxygen accumulation and bio-fouling, make these systems more expensive to build and operate than open systems or semi-closed systems. Photobioreactors can be set up to be continually harvested (as is with the majority of the larger volume cultivation systems), or harvested one batch at a time (for example, as with polyethylene bag cultivation). A batch photobioreactor is set up with, for example, nutrients, microalgae, and water, and the microalgae is allowed to grow until the batch is harvested. A continuous photobioreactor can be harvested, for example, either continually, daily, or at fixed time intervals.

$CO_2$ can be delivered to any of the systems described herein, for example, by bubbling in $CO_2$ from under the surface of the liquid containing the microalgae. Also, sparges can be used to inject $CO_2$ into the liquid. Spargers are, for example, porous disc or tube assemblies that are also referred to as Bubblers, Carbonators, Aerators, Porous Stones and Diffusers.

Nutrients that can be used in the systems described herein include, for example, nitrogen (in the form of $NO_3^-$ or $NH_4$), phosphorus, and trace metals (Fe, Mg, K, Ca, Co, Cu, Mn, Mo, Zn, V, and B). The nutrients can come, for example, in a solid form or in a liquid form. If the nutrients are in a solid form they can be mixed with, for example, fresh or salt water prior to being delivered to the liquid containing the microalgae, or prior to being delivered to a photobioreactor.

The microalgae can be grown in large scale cultures, where large scale cultures refers to growth of cultures in volumes of greater than about 6 liters, or greater than about 10 liters, or greater than about 20 liters. Large scale growth can also be growth of cultures in volumes of 100 liters or more, 500 liters or more, or 1000 liters and up.

Optimal growth temperature is typically about 20° C. to about 25° C., however it is species dependent. According to certain embodiments microalgae cell reach a density of $10^6$ to $10^8$ cells/ml before harvesting.

Post-harvest processing of some sort may be used to prepare the material for oral consumption or as a food composition. Conventional processes typically include at least partial separation of the algal biomass from the liquid culture in which the algae were grown. Optionally, the algal biomass can be homogenized and/or dried to form pellets of various sizes, depending on the target subject and mode of application. Other modes of preparation include spray drying, fluid bed drying, or providing the material as a liquid suspension.

The harvested transgenic microalgae of the present invention per se can form the vaccine or the vaccine can be further formulated into an edible composition further comprising edible diluents, excipients or carriers.

According to certain exemplary embodiments of the invention, the harvested microalgae serve as a food to an intervening organism. According to these embodiments, the intervening organism fed with the transgenic microalgae forms the vaccine. According to certain exemplary embodiments, the intervening organism is a fish food, including, but not limited to, *Artemia* and rotifers. The intervening organism comprising the transgenic microalgae can be harvested by any method as is known in the art, depending on the organism species. The harvested intervening organism can be further processed to form the material of the edible vaccine, for example by drying. According to certain embodiments, the vaccine comprising the intervening organism further comprises edible diluents, excipients or carriers.

The microalgae or the vaccine comprising same can be further formulated to form food compositions or can be used as food additive. According to some embodiments, the edible composition is an animal food composition. According to certain currently specific embodiments, the animal food composition is for feeding aquatic and/or land animals. The following examples are presented in order to more fully illustrate some embodiments of the invention. They should in no way be construed, however, as limiting the broad scope of the invention. One skilled in the art can readily devise many variations and modifications of the principles disclosed herein without departing from the scope of the invention.

EXAMPLES

These Examples relate to specific implementations of at least some aspects of embodiments of the present invention. The Examples are illustrative only and are not intended to be limiting in any way.

Methods

Preparation of NNV Capsid Protein Expressing Vector

The gene encoding for the NNV capsid protein (SEQ ID NO:3) was synthesized according to the codon usage of the alga *Phaeodactylum tricornutum* to obtain the nucleic acid sequence set forth in SEQ ID NO:7.

The synthetic sequence corresponding to 1014 nucleotides encoding for a 37 kDa capsid protein of the NNV virus (the antigen) was cloned into a pPhaT1 vector, into which the sequence encoding vacuolar targeting protein (nucleic acids sequence: SEQ ID NO:6; amino acid sequence SEQ ID NO:1), the HA tag encoding sequence (nucleic acids sequence: SEQ ID NO:14; amino acid sequence SEQ ID NO:13) and optionally the MTS encoding sequence (nucleic acids sequence: SEQ ID NO:12; amino acid sequence SEQ ID NO:11) were cloned previously. The NNV antigen was cloned using BamHI and KpnI. The vacuolar targeting sequence was cloned into pPhaT1 with EcoRI and SacI (producing pPhaT1-Vac). HA tag encoding sequence was cloned into the pPhaT1-Vac using XbaI and SalI. The MTS coding sequence was cloned into pPhaT1-Vac using XbaI and BamHI.

Flagellin Preparation

The gene encoding for the *Salmonella enterica Serovar enteritidis* bacterial flagellin (SEQ ID NO:4) is synthesized according to the codon usage of the alga *Phaeodactylum tricornutum* to obtain the nucleic acid sequence set forth in SEQ ID NO:8. The synthetic sequence corresponding to the bacterial flagellin is cloned into a pPhaT1 vector, to which the vacuolar targeting sequence and the HA tag were sub cloned previously. The bacterial flagellin is cloned using BamHI and KpnI.

The various polynucleotides and constructs of the invention were further cloned under the control of the fcpA promoter and fcpA terminator in the plasmid pPhaT1 (accession number AF219942).

The fcpA promoter is known to be operative in *Phaeodactylum tricornutum*. However, it is to be explicitly understood that other promoters can be used in *Phaeodactylum tricornutum* as well as in other algae.

The vector contains:
An fcpA (fucoxanthin chlorophyll protein A) promoter, upstream to the cloning site of the gene of interest.
MCP—Multiple cloning site.
An fcpB (fucoxanthin chlorophyll protein B) promoter, which controls the transcription of sh ble gene from *Streptoalloteichus hindustanus* encoding a protein that confers zeocine and phleomycin resistance.
fcpA terminators, which appear after (downstream) the gene of interest and after the zeucine resistance gene.
Ampicillin resistant gene.
Origin of replication from *Escherichia coli*.

Algae Culturing and Harvesting

Algae culturing and harvesting was done as described in U.S. Patent Application Publication No. 2011/0081706 to the Applicant of the present invention. Briefly, algae were cultured in filtered sea water enriched with F/2 nutrient for growing diatoms (modified from Andersen R et al. 2005. Recipes for freshwater and seawater media. In: Algal Culturing Techniques (R. A. Andersen, Eds.), pp. 429-538. Elsevier, Amsterdam). F/2 was added every 72 h at a dosage of 1:1000 to the final culture volume. A constant temperature regime was maintained at 21° C. Light:dark was set at 16:8 hours at a light intensity of 100 μmol photons per $m^2 s^1$. $CO_2$ was mixed with air and delivered to the cultures at controlled ratio via the aeration systems. Algae to be used in experiments were harvested near their maximal culture densities. To help flocculation of the algae calcium hydroxide was added to the culture as a fine suspension of particles in water containing 0.15 g/ml $Ca(OH)_2$, and the culture was then filtered or centrifuged. The resulting algae sediment was lyophilized.

Algae Transformation by Particle Bombardment (Performed according to Apt et al. 1996. Mol. Gen Genet. 252:572-579).

Fresh algal culture were grown to mid exponential phase ($2-5*10^6$ cells/ml) in artificial sea water (ASW) F/2 media as described above. 24 hours prior to bombardment cells were harvested, washed twice with fresh ASW+F/2 and resuspended in ⅒ of the original cell volume in ASW+F/2. 0.5 ml of the cell suspension is spotted onto the center of a 55 mm Petri dish containing solidified ASW+F/2 media. Plates are left to dry under normal growth conditions. Bombardment was carried out using a PDS 1000/He biolistic transformation system according to the manufacturer's instructions (BioRad Laboratories Inc., Hercules, Calif. USA) using M17 tungsten powder (BioRad Laboratories Inc.) for cells larger than 2 microns in diameter, and tungsten powder comprised of particles smaller than 0.6 microns (FW06, Canada Fujian Jinxin Powder Metallurgy Co., Markham, ON, Canada) for smaller cells. The tungsten was coated with linear DNA. 1100 or 1350 psi rupture discs were used. All disposables were purchased from BioRad Laboratories Inc. After bombardment the plates were incubated under normal growth conditions for 24 hours after which the cells were plated onto selective solid media and incubated under normal growth conditions until single colonies appeared.

Transformation by Electroporation

Algal cultures were grown to mid exponential phase in artificial seawater (ASW)+F/2 media as described above. Cells were then harvested and washed twice with fresh media. After re-suspending the cells in ⅟50 of the original volume, protoplasts were prepared by adding an equal volume of 4% hemicellulase (Sigma) and 2% Driselase (Sigma) in ASW and were incubated at 37° C. for 4 hours. Protoplast formation was tested by Calcofluor white nonstaining. Protoplasts were washed twice with ASW containing 0.6M D-mannitol and 0.6M D-sorbitol and resuspended in the same media, after which DNA was added (10 μg linear DNA for each 100 μl protoplasts). Protoplasts were transferred to cold electroporation cuvettes and incubated on ice for 7 minutes, then pulsed in an ECM830 electroporation apparatus (BTX, Harvard Apparatus, Holliston, Mass., USA). A variety of pulses is usually applied, ranging from 1000 to 1500 volts, 10-20 msec per pulse. Each cuvette was pulsed 5-10 times Immediately after pulsing the cuvettes were placed on ice for 5 minutes and then the protoplasts were added to 250 μl of fresh growth media (non-selective). After incubating the protoplasts for 24 hours in low light at 25° C. the cells were plated onto selective solid media and incubated under normal growth conditions until single colonies appeared.

Transformation by Microporation

A fresh algal culture was grown to mid exponential phase in ASW+F/2 media. A 10 ml sample of the culture was harvested, washed twice with Dulbecco's phosphate buffered saline (DPBS, Gibco, Invitrogen, Carslbad, Calif., USA) and resuspended in 250 μl of buffer R (supplied by Digital Bio, NanoEnTek Inc., Seoul, Korea, the producer of the microporation apparatus and kit). After adding 8 μg linear DNA to every 100 μl cells, the cells were pulsed. A variety of pulses is typically needed, depending on the type of cells, ranging from 700 to 1700 volts, 10-40 msec pulse length; each sample was pulsed 1-5 times Immediately after pulsing, the cells were transferred to 200 μl fresh culture media (non-selective). After incubating for 24 hours in low light at 25° C., the cells were plated onto selective solid media and incubated under normal culture conditions until single colonies appeared.

Protein Expression Analysis

Analysis of protein expression was performed by SDS-PAGE and Western blot analysis as follows: 20 mg algal powder were lysed in 500 μl Lysis buffer (50 mM Tris pH 7, 1 mM EDTA, 100 mM NaCl, 1.4 mM CHAPS) supplemented with Protease inhibitor cocktail (Sigma; Cat#

P9599) and with 100 µl of acid-washed glass beads (Sigma; Cat#G8772). Protein concentration was determined using BCA Protein Assay Kit (Pierce; Cat#23225) according to manufacturer's instructions and 20 µg of each sample were analyzed by SDS-PAGE (4-20%; Tris-Glicine, Bio-Rad Cat#456-1095) according to manufacturer's instructions. The gel was transferred to PVDF membrane using TransBlot Turbo RTA Transfer Kit (Bio-Rad; Cat#170-4237) according to manufacturer's instructions. The membrane was blocked with blocking buffer (5% skim milk) for 1 hour at ambient temperature and incubated with mouse monoclonal anti HA antibody (Covance; Cat#MMS-101P-1000) for 2 hours at ambient temperature, then washed 3 times with TBS-T (Bio-Rad; Cat#170-6435)+0.02% Tween-20 (Sigma; Cat#P1379). Next, the membrane was incubated with Peroxidase-conjugated AffiniPure Goat Anti-Rabbit IgG (Jackson immunochemicals; Cat#115-035-003) for 1 hour and washed 3 times with TBS-T for 5 minutes at ambient temperature. The membrane was subjected to chemiluminescence using EZ-ECL (Biological Industries; Cat#20-500-120) according to manufacturer's instructions and exposed to Fuji medical X-ray film.

Fish Feed-Algae Mixture

Fish feed is mixed with dried algae (wild type or transgenic) powder. 100 ml of 5% gelatin solution is poured to the algae-fish feed mixture, followed by air drying.

Fish IgM Titer ELISA

Maxisorp 96-well plates (Thermo Scientific; Cat#442404) are coated with 100 µl of 5 µg/ml purified NNV Capsid protein dissolved in coating buffer (0.03M g $Na_2CO_3$ 0.07M $NaHCO_3$ pH 9.6). Following an overnight incubation at 4° C., the plates are washed 3 times with PBS (Biological industries; (Cat#0.2-0.23-5A)+0.05% Tween-20 (Sigma; Cat#P1379)) and blocked with blocking buffer (PBS+1% Bovine Serum Albumin (Sigma; Cat#A7888)) for 1 hour at ambient temperature. Fish sera are serially diluted in PBS and 100 µl of each sample are added to each well and incubated overnight at 4° C. The plate is washed 3 times with washing buffer at room temperature. Then, the plate is incubated at 4° C. overnight with mouse anti fish IgM antibody (LifeSpan Bioscience; Cat#LS-058989). The plate is washed for 3 times with washing buffer and incubated with Peroxidase-conjugated AffiniPure Goat Anti-Mouse IgG (Jackson immunoresearch; Cat#115-035-003) for 1 hour at ambient temperature. Next, the plate is washed 3 times with washing buffer at room temperature and incubated with peroxidase substrate (TMBE; Millipore; Cat# ES001) at ambient temperature. Following the color development, the reaction is terminated with a stop solution (2N $H_2SO_4$). Optical density analysis is performed at 450 nm. The assay is performed in duplicates.

Cytokine Induction after Infection with Betanodavirus

The level of expression of interferon-induced Mx protein is tested after Betanodavirus inoculation using quantitative Real Time PCR (qPCR). Fish are sacrificed and brain, head and kidney are removed aseptically and frozen for RNA and cDNA preparation. qPCR is performed as previously described in Poisa-Beiro et al. (Molecular Immunology, 2008, 45:218-225).

Chickens IgG Titer ELISA

Maxisorp 96-well plates (Thermo Scientific; Cat#442404) are coated with 100 µl of 5 µg/ml purified NNV flagellin dissolved in coating buffer (0.03M g $Na_2CO_3$, 0.07M $NaHCO_3$ pH 9.6). Following an overnight incubation at 4° C., the plates are washed 3 times with PBS (Biological industries; Cat#0.2-0.23-5A)+0.05% Tween-20 (Sigma; Cat#P1379)) and blocked with blocking buffer (PBS+1% Bovine Serum Albumin (Sigma; Cat#A7888) for 1 hour at ambient temperature. Chicken sera are serially diluted in PBS and 100 µl of each sample are added to each well and incubated overnight at 4° C. The plate is washed 3 times with washing buffer at room temperature. Then, the plate is incubated at 4° C. overnight with Rabbit anti-chicken IgG antibody conjugated to horseradish peroxidase (Sigma; Cat# A9046). The plate is washed for 3 times with washing buffer and incubated with a peroxidase substrate (TMBE; Millipore; Cat# ES001) at ambient temperature. Following color development the reaction is terminated with a stop solution (2N $H_2SO_4$). Optical density analysis is performed at 450 nm. The assay is performed in duplicates.

Example 1

Expression of NNV Capsid Protein in Algae Cells

Figure 1:
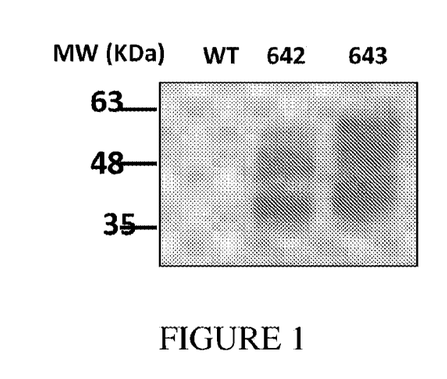
FIG. 1 illustrates expression of the NNV capsid protein in algae cells. Expression was detected in extracts of transformed algae expressing vacuole targeted NNV capsid protein tagged with HA (designated 642) and vacuole-targeted NNV capsid protein tagged with HA and further comprising membrane translocating sequence (MTS) (designated 643). Total protein extracts were analyzed by SDS-PAGE and subjected to Western blot analysis using an anti-HA antibody. Negative control is an extract obtained from wild type (non-transformed) algae.

The NNV capsid protein was fused to a vacuolar targeting sequence and to an HA tag to facilitate the detection of the specific protein in further analyses. Optionally, the capsid protein was fused to the membrane translocating sequence (MTS), in addition to the vacuole leader sequence and the HA tag. The MTS was previously shown by inventors of the present invention to facilitate the absorbance of proteins expressed in algae that were consumed by fish from the fish gut into its blood circulation system. Algae transformants were screened for the NNV recombinant protein expression (FIG. 1). The positive algae clones were further cultivated as described above and the algal material was harvested to be used in the vaccination trials.

Example 2

Vaccination of White Grouper *Epinephelus aeneus* or the European Sea Bass *Dicentrarchus labrax* Larva Fish with NNV Capsid Protein Expressing Algae Three replicates of hatched larvae are used for the vaccination experiments (assay group) and three replicates are used as a control. Fish larvae were kept in tanks supplied with filtered and UV-treated seawater in open circulation (ambient temperature and salinity). Larvae were fed live fry starter feed containing rotifers for 10 days, and then the diet was changed to *Artemia nauplii* for additional 20 days as follows: (1) *Artemia* fed with transgenic algae expressing the vacuole-targeted capsid protein were used for feeding larvae of the assay group; (2) *Artemia* fed with wild-type algae were used for feeding larva of the control group.

Figure 2A:
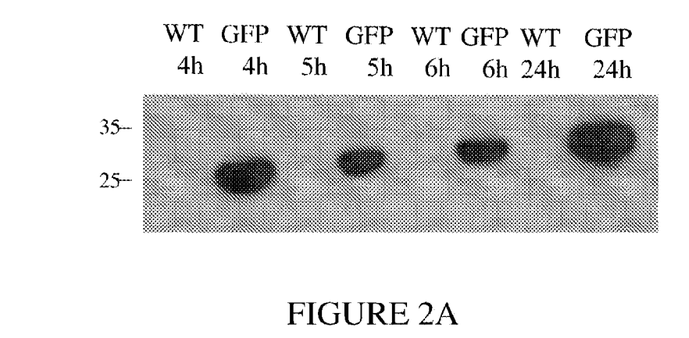
Figure 2B:
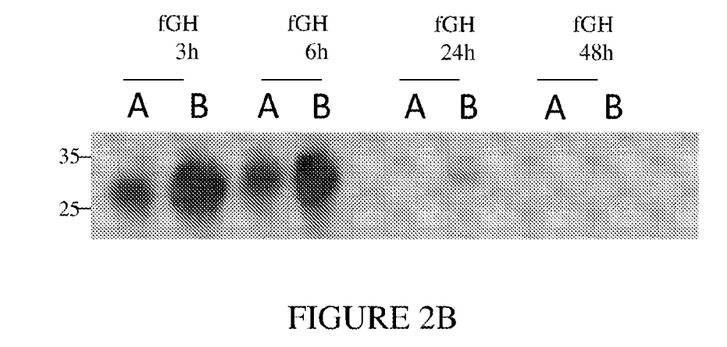
Figure 3A:
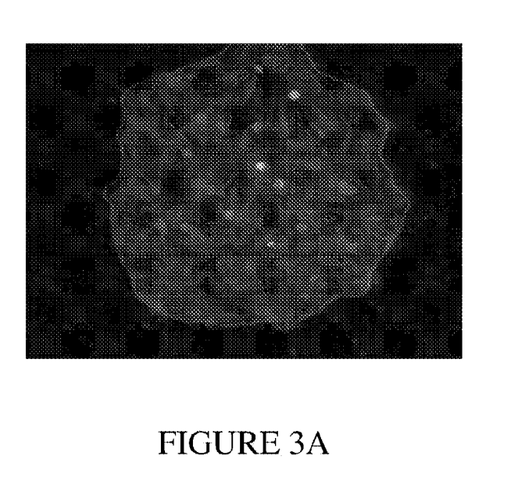
Figure 3B:
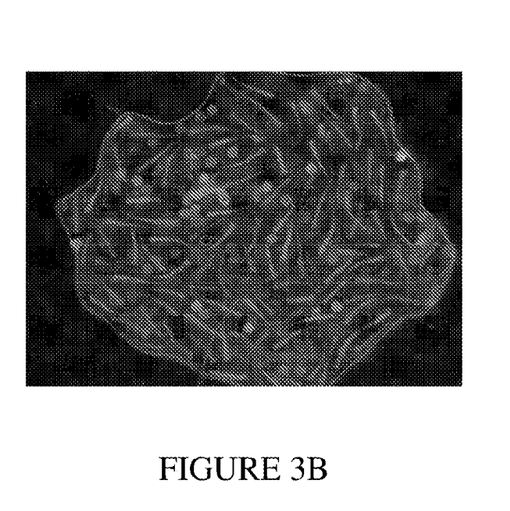

As is demonstrated in FIG. 2 and FIG. 3, vacuole targeted proteins expressed in the transgenic algae can be detected in the *Artemia* body in their intact and functional form at least for 6 hours after feeding. Accordingly, *Artemia* were fed with transgenic algae expressing the vacuole targeted NNV capsid protein or with wild-type algae for 2 hours, and then used immediately for feeding the fish larva of the assay and control groups as described above. When the fish reach about 1 gram body weight and are still vulnerable to NNV, they are transferred to a laboratory aquarium for the challenge trail. About 50% of the larvae of each group (assay and control) are challenged with the virus at a pre-determined LD60 dose by immersion and the other 50% are sham challenged with L-15 media. Challenging is performed as described in Example 4 hereinbelow.

Example 3

Vaccination of White Grouper *Epinephelus aeneus* or the European Sea Bass *Dicentrarchus labrax* Juvenile Fish with NNV Capsid Protein Expressing Algae Larvae are kept in tanks supplied with filtered and UV-treated seawater in open circulation (ambient temperature and salinity). Three replicates of hatched larva are used for the vaccination experiments and three are used as a control (none-vaccination treatment). Larvae were fed live fry starter feed containing rotifers. After 10 days, *Artemia nauplii* which were fed with transgenic microalgae expressing the NNV capsid protein were used for feeding the larvae for additional 20 days (the vaccination experiment, assay group). Larva fed with *Artemia nauplii* which were fed with wild-type algae serve as the control group.

Once larvae are weaned (can be fed with dry fish feed) the NNV capsid protein expressing algae or the wild-type algae are embedded within the fish feed and the feed pellets are used to feed the post larva stage until fingerlings reach 10 gram size. One month post vaccination, about 50% of the vaccinated fish are challenged with the virus by intraperitoneal injection at a predetermined LD60 dose and the other 50% are sham challenged with the L-15 media (Invitrogen). The control group (fed with wild type algae) is also divided to two groups to be challenged with the virus or with the L-15 media as the vaccinated group. Challenging is performed as described in Example 4 hereinbelow.

Example 4

Challenging of Vaccinated Larva and Juvenile Fish with NNV

Three repeats of 10 fingerlings or juvenile fish of the vaccinated group (fed with the transgenic microalgae) and of the non-vaccinated group (fed with the wild-type microalgae) are challenged either by immersion or by intra-peritoneal (IP) injection with $10^7$, $10^5$, $10^3$ or $10^1$ TCID50. Negative controls are sham challenged with L-15 medium supplemented with 5% fetal bovine serum (Invitrogen). The dose causing 60% mortality (LD60) is used for the subsequent challenge. Samplings of 3 fish from each replicate are performed at 0, 15 and 30 days post-challenging. The efficacy of the vaccine is determined by survival rates of the fish following virus challenging, the level of IgM titers in the sera and levels of expression of the cytokine Mx RNA.

Example 5

Vaccination of Chickens with *Salmonella enterica Serovar enteritidis* Flagellin Expressing Algae and Challenging Trials Twenty healthy chicks of 37 days old are assigned to two groups. One group is fed with the flagellin expressing algae, while the control group is fed with wild type algae. Three independent repeats are conducted in parallel. Chicken groups are challenged orally with $10^9$ CFU of *S. enteritidis* at 26 d post-immunization. The cecal droppings are collected at 3, 7, and 14 d post-challenge and the bacterial excretion is examined as described previously in Okamura et al. (Poultry Science 91:2444-2449, 2012). Chickens are subject to necropsy at 18 days post-challenge and the liver, spleen, and cecal contents are examined for *Salmonella*. Sera are also collected before and after vaccination for specific anti-*Salmonella enterica Serovar enteritidis* flagellin antibody titer analysis.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An edible vaccine comprising a transgenic eukaryotic microalga, the transgenic microalga comprising an expression cassette comprising at least one polynucleotide encoding an exogenous antigen further comprising a polynucleotide encoding a vacuolar targeting peptide having the amino acid sequence set forth in any one of SEQ ID NO:1 and SEQ ID NO:9, wherein the encoded exogenous antigen is localized within the vacuole of the microalga cell, and wherein said encoded exogenous antigen induces an immune response in a target subject consuming said vaccine against a disease caused by a pathogen.

2. The edible vaccine of claim 1 wherein the vaccine comprises an intervening organism that ingested the transgenic microalgae.

3. The edible vaccine of claim 1, wherein the antigen is from a pathogen that causes a disease in a fish.

4. The edible vaccine of claim 3, wherein the pathogen is selected from the group consisting of *Streptococcus iniae, Streptococcus agalactiae, Betanodavirus*, and infectious salmon anemia virus.

5. The edible vaccine of claim 4, wherein the pathogen is *Betanodavirus* and the polynucleotide encodes an amino acid sequence at least 90% identical to SEQ ID NO:3.

6. The edible vaccine of claim 1, wherein the antigen is from a pathogen that causes a disease in a poultry subject.

7. The edible vaccine of claim 6, wherein the pathogen is *Salmonella enterica*.

8. The edible vaccine of claim 7, wherein the polynucleotide encodes an amino acid sequence at least 90% identical to SEQ ID NO:4.

9. The edible vaccine of claim 1, wherein the microalga is a marine alga.

10. The edible vaccine of claim 9, wherein the microalga is *Phaeodactylum tricornutum*.

11. An edible composition comprising the edible vaccine of claim 1 further comprising edible diluents, excipients or carriers.

12. An edible composition comprising the edible vaccine of claim 2 further comprising edible diluents, excipients or carriers.

13. The edible composition of claim 12, wherein the intervening organism is selected for the group consisting of *Artemia* and rotifers.

14. A method for oral delivery of an antigen to a subject in need thereof, the method comprising orally administering to the subject an effective amount of a vaccine comprising a transgenic eukaryotic microalga comprising an expression cassette comprising at least one polynucleotide encoding an exogenous antigen further comprising a polynucleotide encoding a vacuolar targeting peptide having the amino acid sequence set forth in any one of SEQ ID NO:1 and SEQ ID NO:9, wherein the encoded exogenous antigen is localized within the vacuole of the microalga cell, and wherein said encoded exogenous antigen induces an immune response in said subject against diseases caused by a pathogen.

15. A method for oral delivery of an antigen to a target animal subject, the method comprising the steps of:
  (a) orally administering to an intervening organism an effective amount of a transgenic microalga comprising at least one polynucleotide encoding exogenous antigen further comprising a polynucleotide encoding a vacuolar targeting peptide having the amino acid sequence set forth in any one of SEQ ID NO:1 and SEQ ID NO:9, wherein the encoded exogenous antigen is localized within the vacuole of the microalga cell, thereby obtaining an intervening organism that have ingested the transgenic microalga; and
  (b) orally administering to the target animal subject an effective amount of the intervening organism that has ingested the transgenic microalga, wherein said encoded exogenous antigen induces an immune response in said target animal subject against disease caused by a pathogen.

* * * * *